US012203926B2

(12) United States Patent
Zenobia et al.

(10) Patent No.: US 12,203,926 B2
(45) Date of Patent: Jan. 21, 2025

(54) ORAL HEALTH MODEL FOR HIGH THROUGHPUT SCREEN AND CHARACTERIZATION OF ORAL HYGIENE PRODUCTS

(71) Applicant: Colgate-Palmolive Company, New York, NY (US)

(72) Inventors: Camille Zenobia, Hampton, NJ (US); Harsh Mahendra Trivedi, Hillsborough, NJ (US); Ying Yang, Monmouth Junction, NJ (US); Carlo Daep, Brooklyn, NY (US); James Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 735 days.

(21) Appl. No.: 17/309,896

(22) PCT Filed: Dec. 17, 2019

(86) PCT No.: PCT/US2019/066791
§ 371 (c)(1),
(2) Date: Jun. 28, 2021

(87) PCT Pub. No.: WO2020/139617
PCT Pub. Date: Jul. 2, 2020

(65) Prior Publication Data
US 2022/0091101 A1 Mar. 24, 2022

Related U.S. Application Data

(60) Provisional application No. 62/785,097, filed on Dec. 26, 2018.

(51) Int. Cl.
*G01N 33/50* (2006.01)
*C12N 1/20* (2006.01)
(Continued)

(52) U.S. Cl.
CPC ........... *G01N 33/5008* (2013.01); *C12N 1/20* (2013.01); *G09B 23/306* (2013.01); *A61K 8/27* (2013.01);
(Continued)

(58) Field of Classification Search
None
See application file for complete search history.

(56) References Cited

FOREIGN PATENT DOCUMENTS

WO 2007/106559 9/2007

OTHER PUBLICATIONS

Bao, Kai; et al; "Establishment of an oral infection model resembling the periodontal pocket in a perfusion bioreactor system" Virulence, 6, 265-173, 2015 (Year: 2015).*
(Continued)

*Primary Examiner* — David W Berke-Schlessel

(57) ABSTRACT

An oral biology model which comprises biofilm, oral epithelial tissue and a suspension of neutrophil-like cells in media is disclosed. The biofilm, which comprises oral bacteria, is produced by culturing oral bacteria on a solid substrate. The oral epithelial tissue may be gingival epithelial tissue to model the gingival crevice or buccal epithelial tissue to model the oral check. The suspension of neutrophil-like cells in media comprises neutrophil-like cells that are differentiated HL60 cells induced to a neutrophil-like phenotype by treatment with retinoic acid. Methods of using the oral biology model to test and compare compounds and formulations or to screen compounds and formulations for their effect on release of inflammatory signals, their effect on biofilm and oral bacteria and/or their effect on the cellular components are disclosed.

9 Claims, 11 Drawing Sheets

(51) Int. Cl.
  *G09B 23/30* (2006.01)
  *A61K 8/27* (2006.01)
  *A61Q 11/00* (2006.01)
  *C12R 1/04* (2006.01)
  *C12R 1/46* (2006.01)

(52) U.S. Cl.
  CPC .......... *A61Q 11/00* (2013.01); *C12N 2513/00* (2013.01); *C12N 2533/18* (2013.01); *C12R 2001/04* (2021.05); *C12R 2001/46* (2021.05)

(56) References Cited

OTHER PUBLICATIONS

Lawson, Nathan D; Berliner, Nancy; "Neutrophil maturation and the role of retinoic acid" Experimental Haematology, 27, 1355-1367, 1999 (Year: 1999).*

Galicia, Johnah; et al; "Neutrophils rescue gingival epithelial cells from bacterial-induced apoptosis" Journal of Leukocyte Biology, 88, 181-186, 2009 (Year: 2009).*

Rudney, JD; Chen, R; "The vital status of human buccal epithelial cells and the bacteria associated with them" Archives of Oral Biology, 51, 291-298, 2006 (Year: 2006).*

Bondy-Carey, Jessica L; et al; "Neutrophils alter epithelial response to Porphyromonas gingivalis in a gingival crevice model" Molecular Oral Microbiology, 28, 102-113, 2013 (Year: 2013).*

Bao et al., 2015, "Establishment of an oral infection model resembling the periodontal pocket in a perfusion bioreactor system", Virulence,6(3):265-273.

Belibasakis et al., 2013, "Interleukin-8 responses of multi-layer gingival epithelia to subgingival biofilms: role of the "Red Complex" species", Plos One, 8(12):e81581.

Brown et al., 2019, "Biofilm-stimulated epithelium modulates the inflammatory responses in co-cultured immune cells", Scientific Reports,9(1).

Guggenheim et al., 2009, "In vitro modeling of host-parasite interactions: the 'subgingival' biofilm challenge of primary human epithelial cells", BMC Microbiology,9(1):280.

International Search Report and the Written Opinion of the International Searching Authority issued in International Application PCT/US2019/066791 mailed Apr. 14, 2020.

Millhouse et al., 2014, "Development of an in vitro periodontol biofilm model for assessing antimicrobial and host modulatory effects of bioactive molecules", BMC Oral Health, 14(1):80.

Murray et al., 2003, "Lipopolysaccharide from the periodontol pathogen porphyromonas gingivalis prevents apoptosis pf HL60—derived neutrophils in vitro", Infection and Immunity,71(12):7232-7235.

Shang et al., 2018, "Multi-species oral biofilm promotes reconstructed human gingiva epithelial barrier function", Scientific reports,8(1).

* cited by examiner

FIG. 11

Table 1: Healthy vs Diseased Biofilm: Treatments with Comp4

| Before Treatment | Healthy Biofilm | Diseased Biofilm |
|---|---|---|
| Streptococcus sp.† | ++++ | + |
| Actinomyces sp.† | ++ | + |
| Porphyromonas sp.* | + | ++++ |
| Prevotella sp.* | + | +++ |
| Aggregatibacter sp.* | + | ++ |

| Treatment with Comp 4 | Healthy Biofilm | Diseased Biofilm | |
|---|---|---|---|
| Streptococcus sp.† | ++++ | +++ | Increase in good bacteria |
| Actinomyces sp.† | +++ | ++ | |
| Porphyromonas sp.* | + | ++ | Reduction in gum disease and odor causing germs after treatment |
| Prevotella sp.* | + | ++ | |
| Aggregatibacter sp.* | + | + | |

† Pathogenic Bacteria
* Beneficial Bacteria

ORAL HEALTH MODEL FOR HIGH THROUGHPUT SCREEN AND CHARACTERIZATION OF ORAL HYGIENE PRODUCTS

BACKGROUND

The gums, also referred to as gingiva, are a part of the soft tissue lining of the mouth that surround the teeth and provide a seal around them. The gingival margin is the interface between the sulcular epithelium and the epithelium of the oral cavity. This interface exists at the most coronal point of the gingiva, otherwise known as the crest of the marginal gingiva. The gingival crevice, also called gingival sulcus, is the space located around a tooth between the wall of the unattached gum tissue and the enamel and/or cementum of the tooth.

Gum disease is an inflammation of the gum line that can progress to affect the bone that surrounds and supports your teeth. The three stages of gum disease—from least to most severe—are gingivitis, periodontitis and advanced periodontitis. Gingivitis is the initial stage of gum disease. The direct cause of gingivitis is plaque—the soft, sticky, colorless film of bacteria that forms constantly on the teeth and gums. If the plaque is not removed by daily brushing and flossing, accumulates and hardens over time.

The bacteria found in this buildup produces toxins that can irritate the gum tissue, causing gingivitis. The immune system is triggered to produce powerful bacteria-fighting elements that attack the infection. Neutrophils, which are a type of granulocyte, are an abundant type of white blood cells that form an essential part of the innate immune system. During the beginning phase of inflammation in the gums, neutrophils are one of the first-responders of inflammatory cells to migrate towards the site of inflammation. The migration of neutrophils is regulated by various chemical signals in a process called chemotaxis. Examples of proteins that induce neutrophil recruitment are include TNF-$\alpha$, RANTES, MIF, GCSF, CXCL10 and GRO. Proteins that can reduce neutrophil recruitment include IL-1Ra and sICAM, and GM-CSF.

An unfortunate consequence is that these elements inadvertently destroy bone and tissue responsible for supporting the teeth. Left untreated, gingivitis can become an advanced stage of gum disease, periodontitis, and cause permanent damage to teeth and jaw. Essentially the body turns on itself. As tissue is broken down, spaces begin to form separating the gums from the teeth. These spaces become infected and deepen, further destroying gum tissue and bone. Eventually when there is an insufficient amount of bone left to support teeth, they begin to feel loose and may have to be removed.

Application of oral care compositions to the oral cavity of an individual can affect the inflammatory signals in the individual's gingival crevice including the reduction of pro-inflammatory signals and the upregulation of signals that reduce inflammation and pro-inflammatory signals. Reducing signals which recruit neutrophils and promoting signals that reduce neutrophil recruitment provides effective strategies to control inflammation and promote healthy gums and overall good oral health. Increasing levels of proteins that reduce neutrophil recruitment such as IL-1Ra, sICAM and GM-CSF in the gingival crevice have an anti-inflammatory effect that reduces the negative consequences of inflammation of the gums. Likewise, reducing levels of proteins that promote neutrophil recruitment such as TNF-$\alpha$, RANTES, MIF, GCSF, CXCL10 and GRO in the gingival crevice have an anti-inflammatory effect that reduces the negative consequences of inflammation of the gums.

BRIEF SUMMARY

An oral biology model is provided which comprises biofilm, oral epithelial tissue and a suspension of neutrophil-like cells in media. The biofilm, which comprises oral bacteria, is produced by culturing oral bacteria on a solid substrate. The oral epithelial tissue may be gingival epithelial tissue to model the gingival crevice or buccal epithelial tissue to model the oral check. The suspension of neutrophil-like cells in media comprises neutrophil-like cells that are differentiated HL60 cells induced to a neutrophil-like phenotype by treatment with retinoic acid. Prior to assembly, the oral epithelial tissue and the biofilm may be treated with a test composition. The oral biology model is assembled by layering the oral epithelial tissue on the suspension of neutrophil-like cells in media and layering the biofilm on the oral epithelial tissue.

Methods of using the oral biology model to test and compare compounds and formulations for their effect on release of inflammatory signals, their effect on biofilm and oral bacteria and/or their effect on the cellular components are provide.

Methods of using the oral biology model to screen compounds and formulations to identify those that have a desirable effect on release of inflammatory signals, on biofilm and oral bacteria and/or on the cellular components are provided.

BRIEF DESCRIPTION OF THE DRAWINGS

FIG. 11 shows data from GCM experiments in Example 2.

DETAILED DESCRIPTION

An oral biology model has been designed for testing biological efficacy of oral health compounds. The model employs a unique combination of cells and bacterial biofilm in an in vitro cell culture that allows for the measure of inflammatory biomarkers that are predictive of clinical effects. The model is predicative of clinical measurements of inflammatory biomarkers (G-CSF, GM-CSF, IL-1RA, TNF-A, VEGF, MMP10, MMP2, MMP9, HSP70, NELA2, MIP-1A, MIP-1B, IL-8, MMP9, MMP3, PGE2), and influence on bacterial communities. The model is in predicting product efficacy.

The oral biology model, which is referred to as the gingival crevice model (GCM) can be used as a model of the gingival crevice by including layered primary gingival epithelial cells or alternatively can be used as a model of oral cheek where the primary cell type changes to a buccal oral epithelial cell layer (as opposed to gingival epithelial cell). Coupled with the layered primary gingival epithelial cells (when modeling the gingival crevice) or layered primary buccal oral epithelial cells (used when the model is adapted as an oral cheek model), the model employs neutrophil-like cells (PMNs, which are HL60 cells induced to a neutrophil-like phenotype with retinoic acid) to simulate what is seen morphologically within healthy junctional gingival tissues or to simulate what would be found in the cheek tissue during abrasion or distress. In addition, an ex vivo derived biofilm, generated from saliva donation and created on substrates, such as HAP disks, poly-D-lysine-coated substrates, collagen-coated substrates, enamel disks, collagen matrices, and polydimethylsiloxane (PDMS), agarose, agar, poly(ethylene glycol) dimethacrylate (PEGDMA) and 2-methacryloyloxyethyl phosphorylcholine polymer (PMPC) hydrogels, is added to the epithelial cell layer. When media used in the cell cultures is not supplemented with serum, the model simulates a non-inflammatory state. To simulate an inflammatory disease-like state within the model system, Fetal Bovine serum may be added. The model allows for rapid analysis of oral care products such as toothpaste, mouthwash, etc.

The GCM is useful to assess product health benefits in a cell culture model that closely mimics a gingival crevice or oral cheek. Proteomics of secreted or expressed proteins, bacterial impact and odor can be evaluated and used to compare the impact of various compounds and compositions. The GCM is useful to test a compound or formulation's ability to prevent or resolve inflammation. The GCM is also useful to predict health or disease status through its use to study oral bacteria and biofilm effects on soft tissue and to test a compound or formulation's effect on oral bacteria and biofilm. The model can also support the testing of individual immune cell function (by saliva donation and isolation of immune cells with histopaque separation techniques) on soft tissue and biofilm to determine health or disease status.

Figure 1:
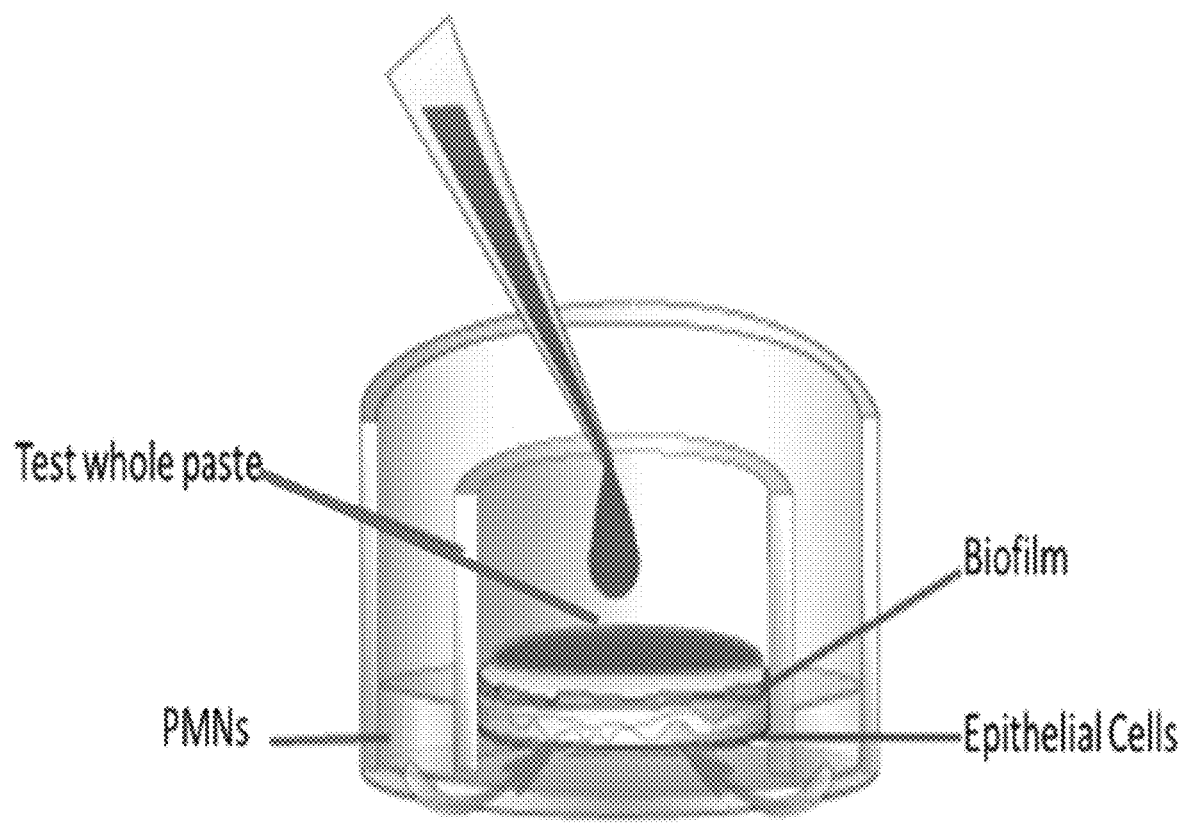
FIG. 1 is an illustration of a GCM.

FIG. 1 contains an illustration of the Gingival Crevice Model (GCM). The GCM combines three components, 1) gingival epithelial cells or buccal oral epithelial cells, 2) neutrophil-like cells, and 3) biofilm that includes oral bacteria.

Gingival Epithelial Tissue or Buccal Oral Epithelial Tissue: There are two types of oral tissue available from MatTek (Ashland, MA): EpiGingival™ gingival epithelium and EpiOral™ buccal oral epithelium. MatTek's EpiGingival and EpiOral tissues consist of normal, human-derived oral epithelial cells. The cells have been cultured to form multilayered, highly differentiated models of the human buccal (EpiOral) and gingival (EpiGingival) phenotypes. The tissues are cultured on specially prepared cell culture inserts using serum free medium. The EpiOral and EpiGin-gival tissue models exhibit in vivo-like morphological and growth characteristics which are uniform and highly reproducible. For traditional GCM, the gingival epithelium is preferred. If a cheek model is the goal, the Oral buccal epithelium is used.

Neutrophil-like cells: HL60 cells (ATCC #CCLO-240) can be induced to differentiate into a neutrophil-like cell types by contacting the HL60 cells with retinoic acid. HL60 cells are maintained at a cell density of $1\times10^5$ cells/mL (Media for HL60 IMEM ATCC #30-2005). Retinoic acid for differentiation of HL60s into neutrophil-like is prepared by dissolving retinoic acid into ETOH to produce a 1 mM solution of retinoic acid in ethanol. When the HL60 cells are to be induced to differentiate into a neutrophil-like cell types by retinoic acid at a concentration of 1 µM (1:1000 dilution of the 1 mM retinoic acid solution), the HL60 cells are brought up to a cell density of $2\times10^5$ cells/mL. Differentiation takes 6 days. Differentiated cells, which make up about 60-80% of cells and are referred to in FIG. 1 as PMNs.

Biofilm: Biofilms are created using saliva cultivated on substrates such as HAP discs, poly-D-lysine, or collagen-coated substrates, or in vivo using enamel in an individually made retainer. In some embodiments, biofilms are created using saliva cultivated on "soft" substrates such as, for example, substrates made from collagen matrices such as CollaForm® Collagen Wound Dressing material (Impladent Ltd., Jamaica, NY), or substrates made from polydimethylsiloxane (PDMS), agarose, agar, poly(ethylene glycol) dimethacrylate (PEGDMA), and 2-methacryloyloxyethyl phosphorylcholine polymer (PMPC) hydrogels. The cultivation of biofilm typically takes 2 days. For example, McBain media supplemented with 5 µg/ml hemin (final concentration) and 1 µg/ml (final concentration) is inoculated with ~2 mL of human saliva. Salivary biofilms are cultured for ~16 hours on substrates, for example HAP disks, under suitable growing conditions such as 37° C. under 5% $CO^2$.

The preparation of each of the components of the GCM is coordinated so the each of the components of the GCM is ready for testing at the same time. Epithelial tissue must be obtained, HL60 cells must be induced with the retinoic acid to differentiate into the neutrophil-like phenotype (PMNs) and the biofilms must be prepared. The preparation of PMNs and biofilms are coordinated so that the PMNs and biofilms are ready following receipt from the supplier and overnight incubation of the MatTek tissue. Upon delivery, the MatTek tissue (epithelial cells) is placed in fresh media in 6 well plates and left to recover overnight in incubator. The GCM is then assembled using the cells induced to a neutrophil-like phenotype (PMNs) and the biofilms.

The GCM can be used to test various test compositions such as mouthwash or toothpaste for example. When testing toothpaste (TP) in the GCM, the product is prepared as a slurry. The TP product is diluted with ultrapure $H_2O$ immediately prior to testing at 1:2 dilution. Mouthwash can be used at full strength. Each of the epithelial tissue and biofilm are treated separately with the same product sample prior to GCM assembly.

MatTek media and, if used, (FBS) serum, are typically used for both epithelial cells and PMNs in the GCM. Prior to assembly, MatTek media and, if used, (FBS) serum are warmed and the epithelial tissue and biofilm are treated separately.

Biofilms are treated once with the test composition, for example, 1:2 (TP:water) toothpaste slurry for 2 minutes at room temperature while shaking at ~100 rpm. Following treatment, the biofilms are washed twice in sterile deionized water at 5 minute intervals and then transferred into fresh sterile water to allow the bacteria to recover at 37° C. for ~3 hours prior to assembly of the GCM and co-incubation with treated cultured epithelial cells.

To treat the MatTek epithelial tissue, the MatTek tissue is removed from the incubator, and each tissue is taken out for treatment with the test composition, for example, 1:2 (TP:water) toothpaste slurry in a 24 well plate. Prior to treatment the media is removed for use a baseline control. Each tissue sample is treated with toothpaste dilution for 2 minutes.

Differentiated HL60s ($2.5 \times 10^5$ cells/mL) are prepared for the GCM by centrifuging 300 RPM for 5 minutes in fresh tubes and re-suspending in MatTek media to model a non-inflammatory condition or MatTek media supplemented with 5% FBS to model an inflammatory condition.

Biofilm and epithelial tissue, which have each been treated with samples of the same test composition such as samples of the same tooth paste dilution, and PMNs are assembled as shown in FIG. 1. The biofilm is layered on the epithelial tissue sample which is layered on the PMN suspension. In some embodiments, the biofilm is completely not in contact with and is isolated from the PMN suspension by the intermediate epithelial tissue layer. The assembled GCM is placed in a bacteria-friendly incubator overnight.

After 24 hours, the various components of the GCM are recovered for analysis. In some embodiments, control experiments (control assays) are run together with experiments testing compositions. Negative control assays use no testing composition or any other material. Positive control assays may use positive control components that have a known effect on the model and/or its component elements.

The media from experiment is harvested and HL60s/PMNs are spun out (300 RPM, 5 min) and frozen/store at –20° C. The collected media may be analyzed to detect and quantify various components using commercially available kits. Examples of such kits FlowCytomix™ kits from eBioscience® (formerly Bender MedSystems®, flow cytometry, non-magnetic beads), the Human Cytokine panel from Invitrogen™ (Luminex®, non-magnetic beads), the Bio-Plex Pro™ X-Plex Custom Assay from Bio-Rad® (Luminex®, magnetic beads) and (iv) the MILLIPLEX® Kit from Millipore™ (Luminex®, magnetic beads). Multiplex kits with magnetic beads (Luminex®) from Invitrogen™ and BD™ Cytometric Bead Array (CBA) Human Enhanced Sensitivity kits (flow cytometry, non-magnetic beads) can be used. For example, cytokine/chemokines such as MIF, MIP-la, CXCL1, CXCL5, CXCL8, CXCL2 and CXCL6, are detected in the recovered media and quantified using Milliplex MagPix kits.

Bacterial analysis can be performed on biofilms on HAP discs, poly-D-lysine, or collagen-coated substrates, enamel, collagen matrices, and polydimethylsiloxane (PDMS), agarose, agar, poly(ethylene glycol) dimethacrylate (PEGDMA) and 2-methacryloyloxyethyl phosphorylcholine polymer (PMPC) hydrogels. Alternatively, the biofilms can be stored in –80 C for later analysis.

PMNs can be recovered for analysis. After removing supernatant from cells, the cells are washed two times in cold PBS (300 RPM, 5 min). The PMNs are brought up in 200 µL of fixation buffer (room temp for 10 min or overnight at 4 C) and stained with desired antibody staining procedure.

MatTek tissue can be evaluated after treatment. MTT assay should be done if there is question about cellular toxicity. The tissue is fixed for histological analysis if the location of protein expression is to be assessed. Tissue may be sonicated and analyzed for cytokine analysis if the protein of interest is not secreted.

The use of the HL60-derived PMN, as a substitute for isolated neutrophils, provides a consistent, easy to obtain, source of cells with the neutrophil phenotype. Fresh human granulocytes, which include a spectrum of cells undergoing apoptosis when isolated from the blood, must be re-isolated on a daily basis.

The use of biofilm in the GCM provides several advantages. It allows for a better simulation of the oral biome, particularly when provided as an ex vivo sample derived from saliva donation. Moreover, the preparation of the biofilm on a substrate allows its use in the GCM assembly to remain more effectively layered over the epithelial layer and separate from the neutrophil-like cell suspension.

The GCM can be used to compare the effects of different formulations on one or more components of the GCM, such as the PMNs, the epithelial tissue, the biofilm and/or the microbes within the biofilm. The GCM can be used to screen test compositions which may be compounds or formulations to identify those that have desirable effects of on one or more components of the GCM, such as the PMNs, the epithelial tissue, the biofilm and/or the microbes within the biofilm. The GCM may be used to perform time studies in which effects are determined over time by initially running multiple identical assays and collected data from assays at different time points to compare effects over time. The GCM may be used to perform concentration studies in which multiple assays are run with the same test composition used at different concentrations in different individual assays.

EXAMPLES

Example 1

The GCM was used to evaluate toothpaste compositions including Composition 1 (Comp1), Composition 2 (Comp2) and Composition 3 (Comp3). Composition 1 comprises zinc oxide, zinc citrate and stannous fluoride. Zinc oxide was present in the composition at about 1%. Zinc citrate was present in the composition at about 0.5%. Stannous fluoride was present in the composition at about 0.5%. Composition 2 comprises zinc oxide, zinc citrate, stannous fluoride and arginine. Zinc oxide was present in the composition at about 1%. Zinc citrate was present in the composition at about 0.5%. Stannous fluoride was present in the composition at about 0.5%. Arginine was present in the composition at about 1.5%. Composition 3 comprises zinc oxide, zinc citrate, stannous fluoride and zingerone. Zinc oxide was present in the composition at about 1%. Zinc citrate was present in the composition at about 0.5%. Stannous fluoride was present in the composition at about 0.5%. Zingerone was present in the composition at about 0.1-0.3%.

Data from the GCM experiment is shown in FIGS. 2-7. In each figure, control corresponds to the negative control. Pos1-Pos4 refer to control formulations. Comp1, Comp2 and Comp3 correspond to the tested compositions Composition 1, Composition 2 and Composition 3, respectively. IL-1RA (FIG. 2), CXCL10 (FIG. 3), ICAM-1 (FIG. 4), G-CSF (FIG. 5), TNFa (FIG. 6) and RANTES (FIG. 7) levels in response to the treatment with the various formulations were measured.

Figure 2:
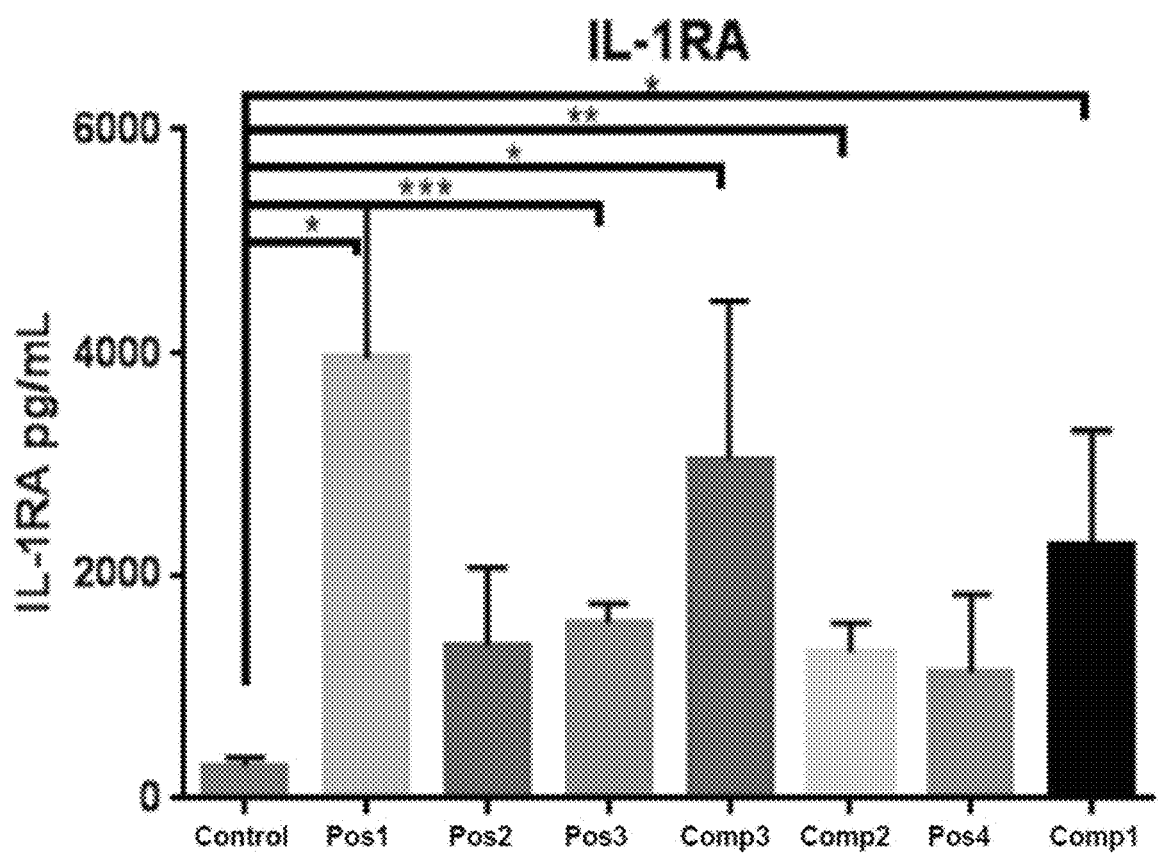
FIG. 2 shows data from GCM experiments in Example 1 comparing IL-1RA levels in response to treatment with various formulations.
Figure 3:
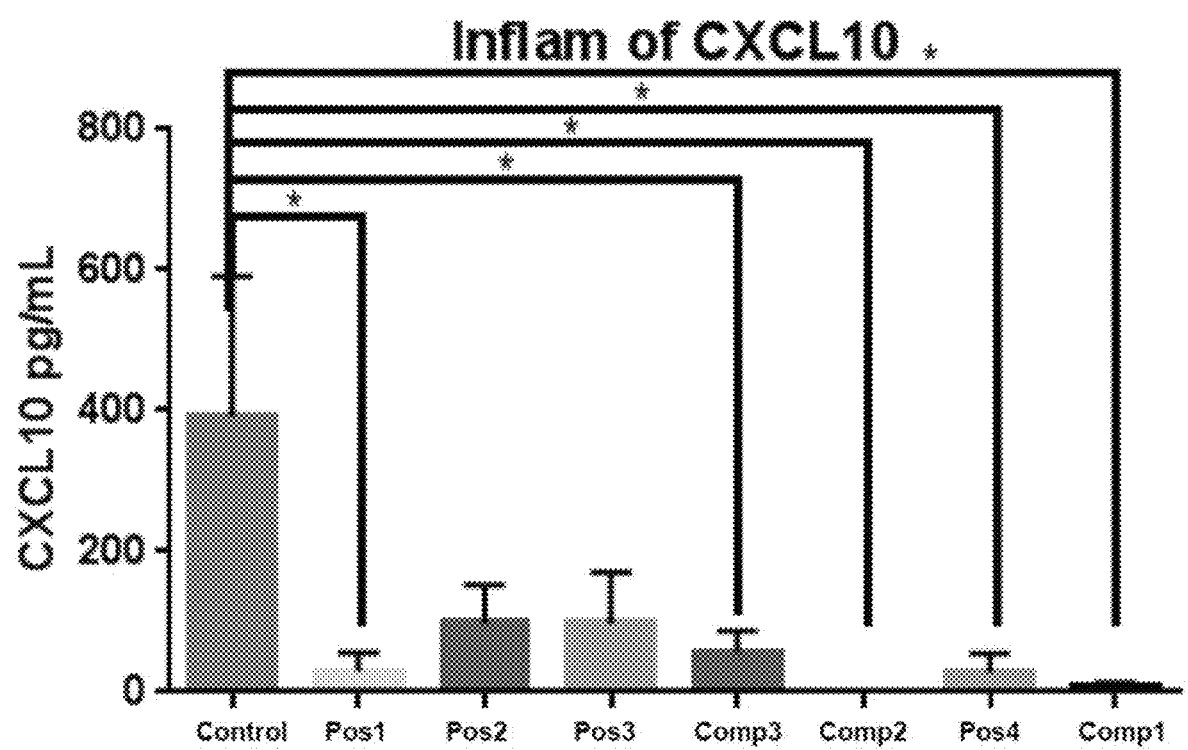
FIG. 3 shows data from GCM experiments in Example 1 comparing CXCL10 levels in response to treatment with various formulations.
Figure 4:
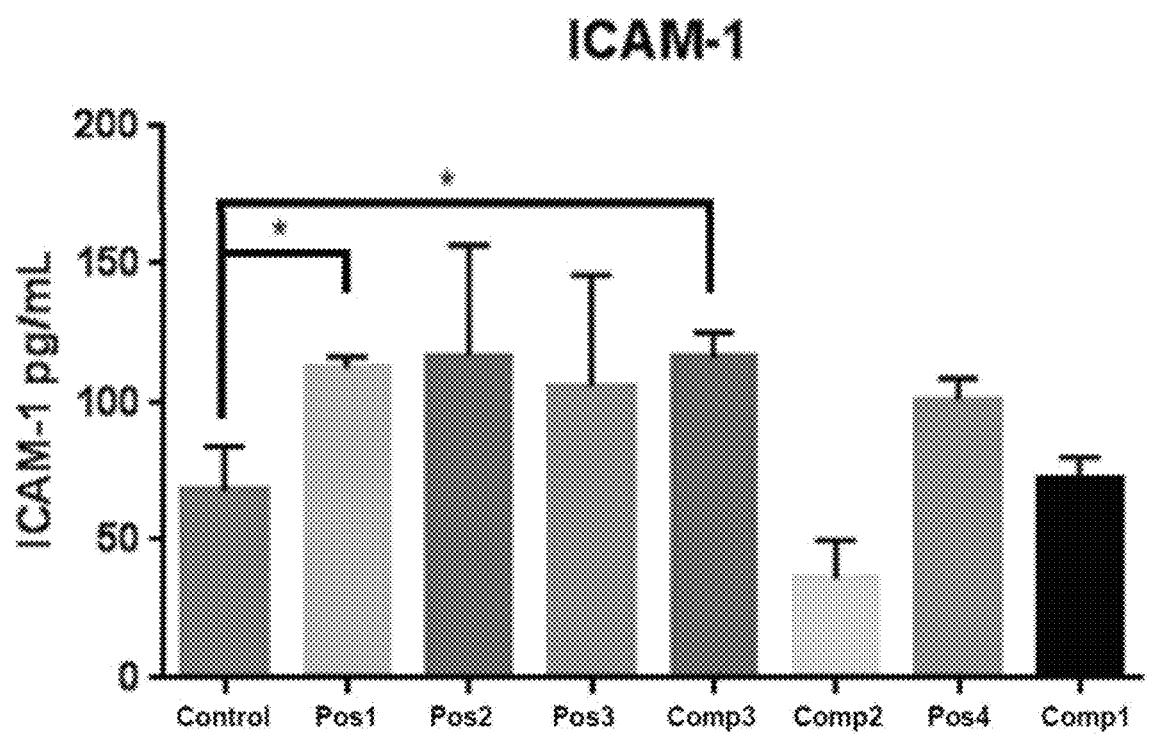
FIG. 4 shows data from GCM experiments in Example 1 comparing ICAM-1 levels in response to treatment with various formulations.
Figure 5:
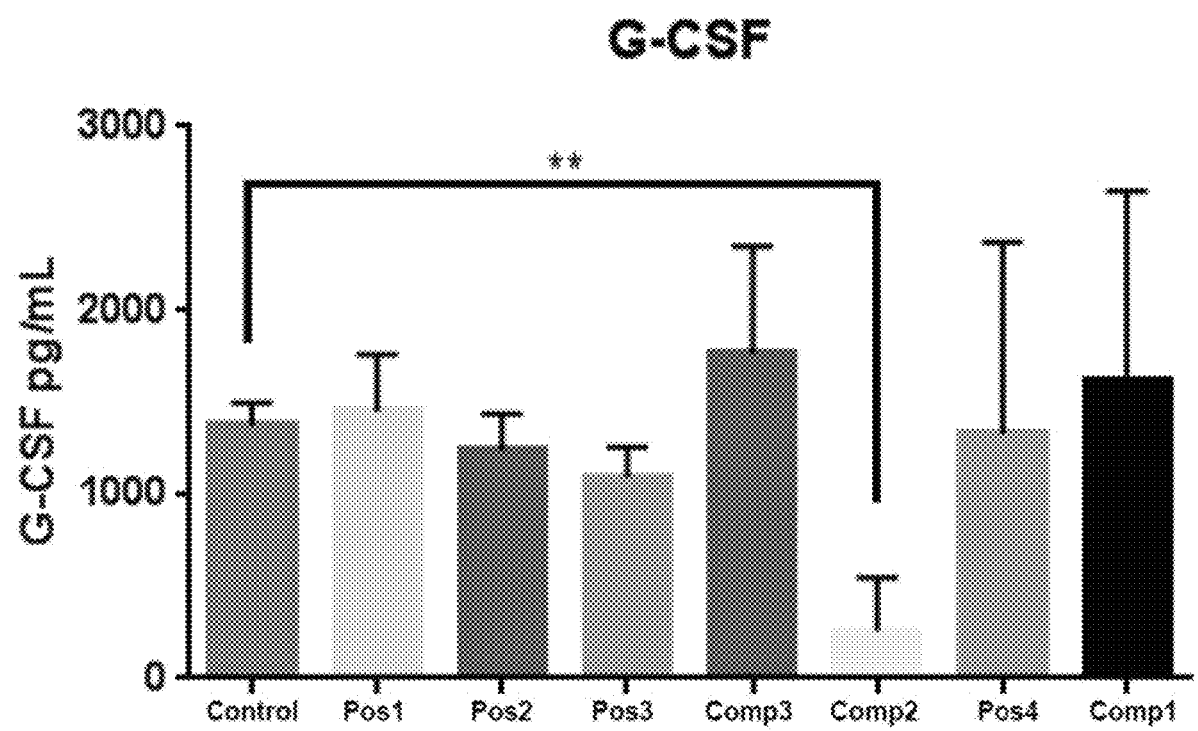
FIG. 5 shows data from GCM experiments in Example 1 comparing G-CSF levels in response to treatment with various formulations.
Figure 6:
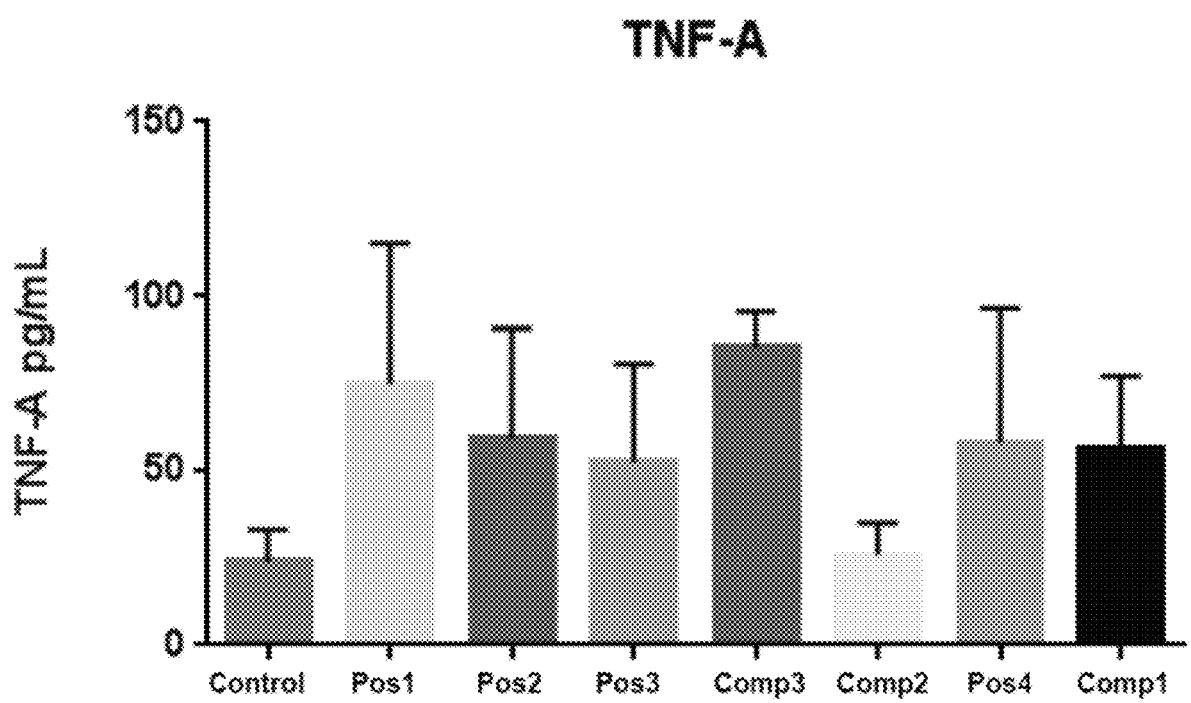
FIG. 6 shows data from GCM experiments in Example 1 comparing TNF$\alpha$ levels in response to treatment with various formulations.

As shown in FIGS. 2 and 3, results of treatment in the GCM with Composition 1 showed an induction of IL-1Ra (FIG. 2), which is a protein that reduces signals associated with neutrophil recruitment, and a reduction of CXCL10 (FIG. 3), which is a protein that promotes neutrophil recruitment. As shown in FIGS. 2, 3 and 5, results of treatment in the GCM with Composition 2 showed an induction of IL-1Ra (FIG. 2), which is a protein that reduces signals associated with neutrophil recruitment, and a reduction of CXCL10 (FIG. 3) and G-CSF (FIG. 5), which are proteins that promote neutrophil recruitment. As shown in FIGS. 2, 3 and 4, results of treatment in the GCM with Composition 3 showed an induction of IL-1Ra (FIG. 2) and sICAM (FIG. 4), which are proteins that reduce signals associated with neutrophil recruitment, and a reduction in levels of CXCL10 (FIG. 3), which is a protein that promotes neutrophil recruitment.

Figure 7:
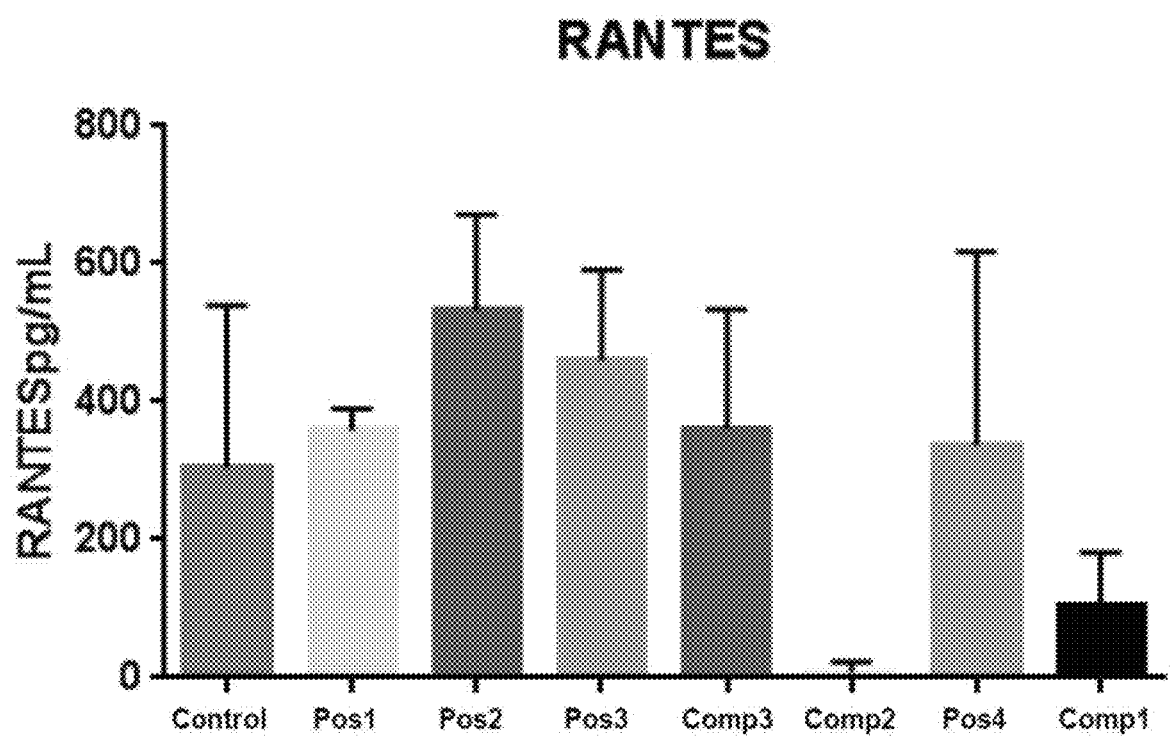
FIG. 7 shows data from GCM experiments in Example 1 comparing RANTES levels in response to treatment with various formulations.

Composition 2 reduced G-CSF (FIG. 5), which is one of the main neutrophil chemokines and is involved in a key inflammatory pathway that has been shown to be important in the progression of periodontal disease. Composition 2 showed a trend in reduction of additional neutrophil chemokines/inflammatory cytokines including TNF-A (FIG. 6) and RANTES (FIG. 7).

Example 2

Figure 8:
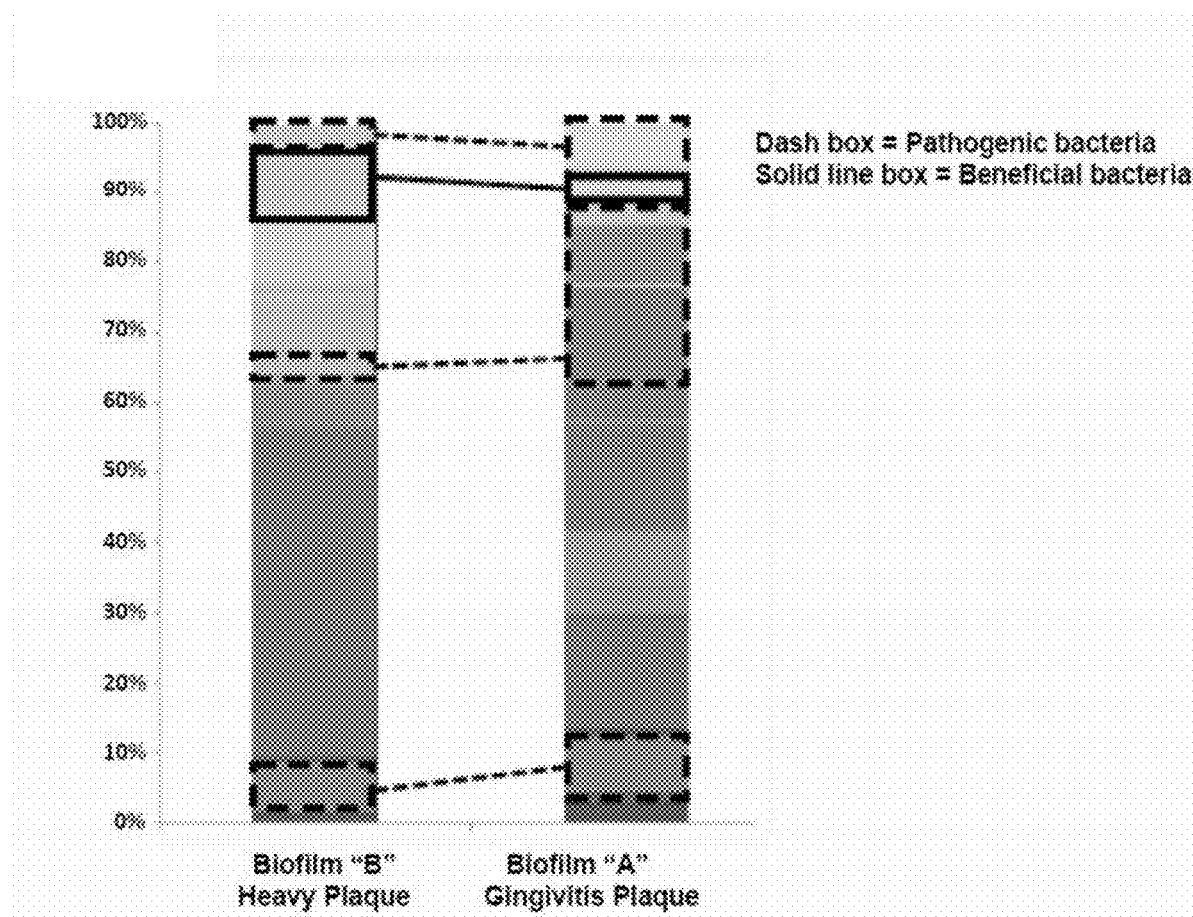
FIG. 8 illustrates the bacterial composition of two biofilms: one from a healthy individual and one from an individual with gingivitis.

The GCM was used to evaluate a toothpaste composition, Composition 4 (Comp4), which comprises zinc oxide, zinc citrate and arginine. Zinc oxide was present in the composition at about 1%. Zinc citrate was present in the composition at about 0.5%. Arginine was present in the composition at about 1.5%. Data from the evaluation is shown in FIG. 8 and Table 1.

The GCM was used to look at impacts on bacterial communities. Specifically, experiments were undertaken to evaluate how toothpaste compositions including Composition 4 treatment impacts the microbiome. Two different biofilms were acquired, one from healthy person and one from healthy person with gingival disease. FIG. 8 illustrates a comparison of the composition of the two biofilms. Biofilm "A" represents the biofilm from the healthy person who has gingival disease. Biofilm "B" represents the biofilm from the healthy person who does not have gingival disease. The Dash boxes correspond to the percentage of different species of pathogenic bacteria. The Solid line box corresponds to the percentage of a species of beneficial bacteria. Compared to the biofilm from the healthy person who does not have gingivitis, the biofilm from the healthy person who has gingival disease has larger percentages of each species of pathogenic bacteria and a smaller percentage of beneficial bacteria.

FIG. 11 shows data from GCM experiments performed using the biofilm from the healthy person who does not have gingival disease (Healthy Biofilm) and the biofilm from the healthy person who has gingival disease (Diseased Biofilm). Those data from the GCM experiments, which compared of Healthy Biofilm vs Diseased Biofilm, demonstrates that treatments with Composition 4 show shift towards health. The amount of two beneficial oral bacteria species (*Streptococcus* sp. and *Actinomyces* sp.) and the amount of three pathogenic oral bacteria species (*Porphyromonas* sp., *Prevotella* sp. and Aggregatibacter sp.) were scored in each of the Healthy Biofilm and Diseased Biofilm before treatment with Composition 4 and after treatment with Composition 4. In both instances, after treatment with Composition 4 the overall bacterial load was reduced and there was a shift in microbial profile of the pathogenic bacteria toward beneficial bacteria. In the Diseased Biofilm, the shift from pathogenic bacteria toward beneficial bacteria was substantial with an increase in beneficial bacteria and a reduction in pathogenic bacteria.

Example 3

Figure 9:
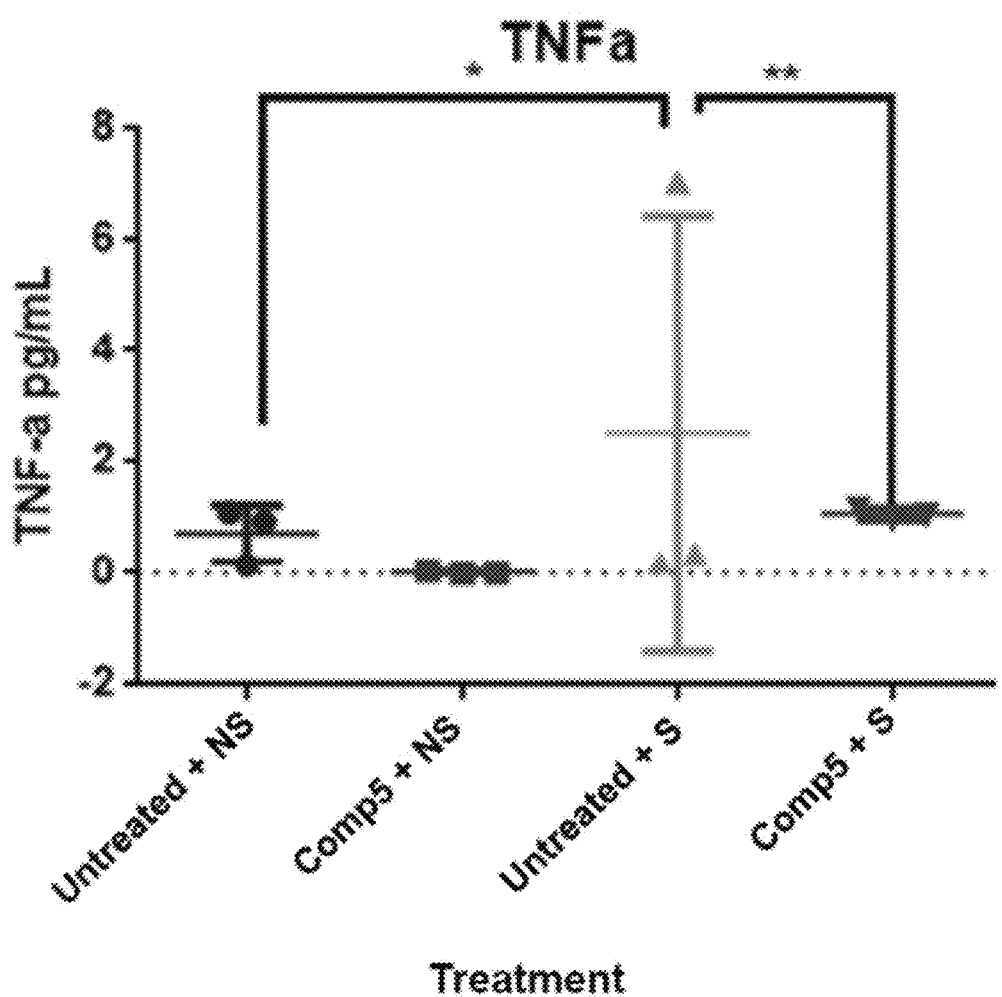
FIG. 9 shows data from GCM experiments in Example 3 comparing TNF$\alpha$ levels in response to treatment with a toothpaste formulation.
Figure 10:
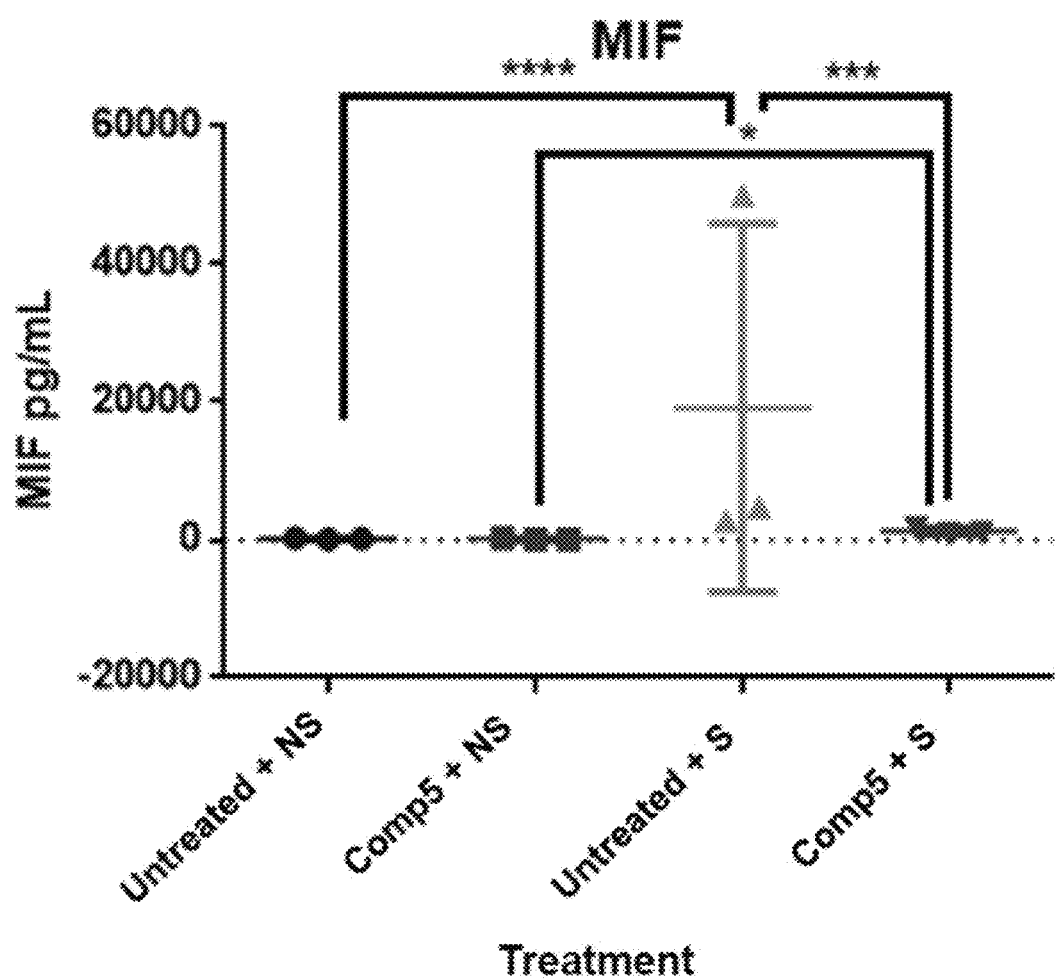
FIG. 10 shows data from GCM experiments in Example 3 comparing RANTES levels in response to treatment with a toothpaste formulation.

The GCM was used to evaluate toothpaste composition, Composition 5 (Comp5), which comprises Fluoride (0.454% $SnF_2$) and Zinc Phosphate (1.0% $Zn_3(PO_4)_2$). Data from the GCM experiment is shown in FIGS. 9 and 10.

The invention claimed is:

1. An oral biology model comprising:
   a) biofilm that comprises oral bacteria, wherein the biofilm is produced by culturing oral bacteria on a solid substrate;
   b) oral epithelial tissue selected from the group consisting of gingival epithelial tissue and buccal epithelial tissue;
   c) a suspension of neutrophil-like cells in media that comprises neutrophil-like cells that are differentiated HL60 cells induced to a neutrophil-like phenotype by treatment with retinoic acid;
   wherein the oral epithelial tissue is layered on the suspension of neutrophil-like cells in media and the biofilm is layered on the oral epithelial tissue, and the biofilm is not in contact with the suspension of and is isolated from the neutrophil-like cells.

2. The oral biology model of claim 1 wherein the biofilm is produced by culturing a saliva donation that comprises oral bacteria on a solid substrate.

3. The oral biology model of claim 2 wherein the solid substrate is selected from the group consisting of: a hydroxyapatite (HAP) disc, a poly-D-lysine coated substrate, a collagen-coated substrate, an enamel substrate, a collagen matrix substrate, a polydimethylsiloxane substrate, an agarose hydrogel, an agar and poly(ethylene glycol) dimethacrylate (PEGDMA) hydrogel, and a 2-methacryloyloxyethyl phosphorylcholine polymer (PMPC) hydrogel.

4. The oral biology model of claim 1 wherein the oral epithelial tissue is gingival epithelial tissue.

5. The oral biology model of claim 1 wherein the oral epithelial tissue is buccal epithelial tissue.

6. The oral biology model of claim 1 wherein the media is serum free media.

7. The oral biology model of claim 1 wherein the media is supplemented with fetal bovine serum.

8. The oral biology model of claim 1 wherein the oral epithelial tissue is treated with a sample of a test composition prior to being layered on the suspension of neutrophil-like cells in media and the biofilm is treated with a sample of the test composition prior to being layered on the oral epithelial tissue.

9. The oral biology model of claim 8 wherein the test composition is selected from the group consisting of: a mouthwash formulation and a dilution of a toothpaste formulation.

* * * * *